US008454555B2

(12) United States Patent
Struijk et al.

(10) Patent No.: US 8,454,555 B2
(45) Date of Patent: Jun. 4, 2013

(54) CARDIAC RELATED NEURAL ACTIVITY (75) Inventors: Johannes Jan Struijk, Terndrup (DK);
Cristian Sevcencu, Aalborg Ø (DK);
Kristian Rauhe Harreby, Aalborg (DK)

(73) Assignee: Aalborg Universitet, Aalborg (DK)

( * ) Notice: Subject to any disclaimer, the term of this patent is extended or adjusted under 35 U.S.C. 154(b) by 102 days.

(21) Appl. No.: 13/119,761

(22) PCT Filed: Sep. 18, 2009

(86) PCT No.: PCT/DK2009/050245
§ 371 (c)(1),
(2), (4) Date: May 5, 2011

(87) PCT Pub. No.: WO2010/031406
PCT Pub. Date: Mar. 25, 2010

(65) Prior Publication Data
US 2011/0224602 A1    Sep. 15, 2011

(30) Foreign Application Priority Data
Sep. 19, 2008   (DK) .................................. 2008 01313

(51) Int. Cl.
*A61M 31/00*    (2006.01)
(52) U.S. Cl.
USPC ........................... 604/66; 604/891.1; 600/483
(58) Field of Classification Search
USPC   604/65–67, 131, 151, 890.1, 891.1; 600/483; 607/45
See application file for complete search history.

(56) References Cited

U.S. PATENT DOCUMENTS

| 5,609,158 | A | 3/1997 | Chan |
| 2006/0122525 | A1 | 6/2006 | Shusterman |
| 2007/0100392 | A1 | 5/2007 | Maschino et al. |
| 2007/0238939 | A1 | 10/2007 | Giftakis et al. |
| 2008/0027346 | A1 | 1/2008 | Litt et al. |

FOREIGN PATENT DOCUMENTS
EP    0688578 A   12/1995

OTHER PUBLICATIONS

International Search Report from International Application No. PCT/DK2009/050245 mailed on Dec. 9, 2009.
Birkett, C. L., et al., "A Signal-Averaging Technique for the Analysis of Human Muscle Sympathetic Nerve Activity," *Journal of Applied Physiology*, American Physiological Society, US, vol. 73, Jan. 1, 1992.
Halliwill, J. R., et al., "Segregated Signal Averaging of Sympathetic Baroreflex Responses in Humans," J. Appl. Physiol., vol. 88, pp. 767-773, 2000.

*Primary Examiner* — Theodore Stigell
(74) *Attorney, Agent, or Firm* — Pearl Cohen Zedek Latzer LLP (57) ABSTRACT The present invention relates to a medical device for analyzing cardiac related input signals. The device is capable of receiving an ECG-signal and a nerve activity signal, such as vagus nerve signal in order to detect a cardiac related neural activity, such as epilepsy. The device is programmed for detecting a trigger feature (e.g. the R-peak) in the signal and extracting a nerve activity signal segment from the nerve activity signal in response to detecting the trigger feature. An activity related feature is generated either based on a combined signal obtained from a number of nerve activity signal segments, or as a segment-based activity related feature obtained from a number of nerve activity signal segments. Moreover, the device is adapted for comparing the activity related feature to a predefine criterion in order to detect the cardiac related neural activity.

14 Claims, 5 Drawing Sheets

CARDIAC RELATED NEURAL ACTIVITY

CROSS-REFERENCE TO RELATED APPLICATIONS

This application is a National Phase Application of PCT International Application No. PCT/DK2009/050245, International Filing Date Sep. 18, 2009, claiming priority of Danish Patent Application No. PA 2008 01313, filed Sep. 19, 2008.

FIELD OF THE INVENTION

The present invention relates to a medical device for analyzing cardiac related input signals. Moreover, the invention relates to a computer program product and to a method for detecting cardiac related neural activity.

BACKGROUND OF THE INVENTION

Epilepsy is a common chronic neurological disorder that is characterized by recurrent seizures. Epileptic seizures are characterised by a hyper synchronization of neural activity in the brain, which may be accompanied by involuntary movement, loss of consciousness and changes in the autonomic control. Epilepsy typically cause major problems for patients suffering from this disease or disorder. Over the years, several treatment methods have been developed to minimize the symptoms or to treat the disease.

There exist several approaches related to dealing with epilepsy. One way relates to predicting a forthcoming seizure by awareness of the patient to the symptoms. This is not very reliable and there may not be enough time for the patient to start a treatment or to alarm another person before the seizure sets in.

It is also possible to schedule different forms of stimulation to prevent a seizure e.g. by the use of scheduled intake of medication or scheduled electrical neuro-stimulation. In both cases scheduled stimulation can result in over- or under stimulation, which can be harmful to the patient. In connection with neuro-stimulation different devices have been developed which are able to (directly or indirectly) electrically stimulate the brain of the patient to prevent seizures.

In the published US patent application no. 2007/0100392 A1 a method and a device for treating epilepsy is disclosed. In the disclosed method, deep brain stimulation is combined with vagus nerve stimulation to enhance symptomatic relief of the disorder. Deep brain stimulation requires serious invasive procedure in the brain which may be problematic.

In the published US patent application no. 2008/0027346 A1 a method and a device capable of recording and predicting epileptic seizures is disclosed with the motivation of replacing invasive procedures. In the disclosure, spontaneous and/or evoked electrical, chemical or other brain activity from a particular region of the brain are monitored via an electrode that is placed on, through or inside e.g. cranial nerves.

Nevertheless, there is still a need in the art for improvements of seizure related treatment devices.

SUMMARY OF THE INVENTION

The inventors of the present invention have realized that there is a need for improved means for analyzing cardiac related neural activity for the treatment of neurological disorders, such as epilepsy, as well as for other disorders or conditions which may be detected via nerve recordings. Examples of this include chronic heart failure and other heart conditions.

In particular, a device and method capable of reliably predicting seizures would be advantageous. In other aspects, a device or method which is capable of stimulating the patient and thereby preventing seizures, where the stimulation is based on a reliable prediction, would be advantageous.

To this end, in a first aspect, the invention relates to a device for analyzing cardiac related neural activity, the device comprises:
  an input unit for receiving an ECG-signal and a nerve activity signal;
  a signal treatment unit programmed for:
    detecting a trigger feature in the ECG-signal,
    in response to detecting a trigger feature, extracting a nerve activity signal segment from the nerve activity signal,
  an extraction unit programmed for:
    generating a combined signal from a number of nerve activity signal segments and
    extracting an activity related feature from the combined signal; or
    extracting a segment-based activity related feature from a number of nerve activity signal segments, thereby extracting a number of activity related features and
    generating an activity related feature by combining the segment-based activity related features;
  a monitoring unit programmed for:
    comparing the activity related feature to a predefined criterion and in the event of the activity related feature fulfils the predefined criterion, detecting the cardiac related neural activity.

The invention is particularly, but not exclusively, advantageous for providing a device capable of analyzing cardiac related neural activity. Neural signals comprise signals related to the number of activities in which the nerve is involved. Extracting specific organ related activity features is not a straight forward task. The present invention is capable of extract cardiac related features from a general nerve signal. This may enable early detection or form a solid base for prediction or detecting symptoms of neural disorders or other diseases, including but not limited to epilepsy.

The invention may be used for controlling on-demand treatment of neural disorders such as epileptic seizures or for controlling a seizure alarm.

The cardiac related neural activity is based on correlating segments of the nerve activity signal by use of electrical heart signal (Electrocardiogram-ECG) trigger features. The trigger feature may be the R-peak of the ECG-signal since this is typically the most prominent feature of the ECG. Other features in the ECG may be used as a trigger feature e.g. the P wave, the Q wave, the S wave, the T wave or one or more of the intervals in between any of the waves.

The recorded nerve activity signal may be recorded via methods where the activity of a fraction of fibres or of the whole nerve is recorded e.g. using electrodes inserted into the nerve or cuff electrode which encloses the nerve.

The ECG may be obtained with any relevant method. The ECG may be recorded from electrodes on or incorporated in the casing of the implantable device, from the nerve activity signal electrode, the wire between the device and the electrode or a combination of these.

In the device, the ECG-signal and the nerve activity signal, that is the input signals, are received at an input unit. The input unit may be any suitable means for receiving signals.

The input signals are treated by a signal treatment unit, typically in the form of suitable computing unit. In the signal treatment unit, a trigger feature is detected and in response to detecting the trigger feature, a segment of the nerve activity signal is extracted, typically in terms of extraction of a signal segment extending at both sides of the trigger feature and including the trigger feature. In an activation unit, the extracted nerve activity signal segments may then be combined to form a single combined signal, the activity related feature is extracted based on the combined signal. In an alternative embodiment, the order of the steps are changed, so that a segment-based activity related feature is extracted from each of the nerve activity signal segments, the activity related features is generated by combining the segment-based activity related features. At a monitoring unit the activity related feature is evaluated against a predefined criterion indicative of a predefined desired behaviour of the neural activity. The activity related feature may be selected based on supervised or unsupervised classification. The classification features may be evaluated based on their capability of predicting or detecting a specific behaviour of the cardiac related neural activity, such as the capability of predicting or detecting a specific symptom of a given disorder. The device may continuously analyse the input signals in order to provide online analysis of the cardiac related neural activity.

The activity related feature may include, but is not limited to: absolute values, timing of a max or min value or the frequency of a min or max value. Features may also be defined as a difference between e.g. a running baseline interval occurring prior to a current interval, or by comparing features extracted from several nerves.

In general, the nerve activity signal may relate to any nerve which carries cardiac related activity. Relevant nerves may be nerves related to sensory (baro receptors) and motor (controlling the heart) nerve fibres. Moreover relevant nerves may relate to autonomic nerves such as: the vagus nerve (10th cranial nerve) and the glossopharyngeus nerve (9th cranial nerve) from the parasympathetic system and to the superior cervical cardiac nerve, middle cervical cardiac nerve, inferior cervical nerve and the thoracic cardiac branch from the sympathetic system. Of particular interest is the vagus nerve, since stimulation of the vagus nerve is known in the art. The nerve activity signal may also relate to a blood pressure signal such as a signal from the baro receptors in the carotid sinus nerve or in the aortic depressor nerve.

In an embodiment, the signal treatment unit may further be programmed for pre-processing the nerve activity signal and basing the combined signal on the pre-processed nerve activity signal or extracting the segment-based activity related features from the pre-processed nerve activity signal. The pre-processing may comprise filters, such as digital or analogue filters e.g. high pass or low pass filters. The nerve activity signal may be processed or transformed to any representation e.g. time, time-frequency, wavelet etc., before, during or after the generation of a combined signal from the number of nerve activity signal segments. In embodiments, the extraction of the activity related feature is done from the pre-processed signal.

The combined signal may be generated by a functional mapping of the number of signal segments to the combined signal. The mapping may be a functional transformation of each sample point in the nerve activity signal segments to a combined sample point in the combined signal. The functional mapping may be a mathematical processing method which include, but is not limited to: averaging, trimmed mean, median, standard deviation, variance, measures of correlation, independent component analysis. In the same way may the combining of the segment-based activity related features be performed by use of a mathematical processing method which include, but is not limited to: averaging, trimmed mean, median, standard deviation, variance, measures of correlation, independent component analysis.

The predefined criterion may be set as a static measure, e.g. in terms of a threshold of the activity related feature. The behaviour of the activity related feature may be known in absolute terms enabling the use of such a criterion. Alternatively, the predefined criterion may be adaptively modified during the measurement of the input signals. In this situation, the predefined criterion defines predefined rules as to when the criterion is met.

The signal treatment unit may be further programmed for evaluating the nerve activity signal segment by use of an evaluation algorithm, and in accordance with an output of the evaluation algorithm accepts or rejects the nerve activity signal segment. Nerve activity signal recordings with extensive noise caused by e.g. contraction of surrounding muscle tissue, movement artefacts or other sources, may be rejected to further analysis by noise rejection algorithms implemented in either software or hardware. The rejection of the nerve activity signal may also be based on other inputs, e.g. the respiration phase generates muscle-related signal contribution in the nerve activity signal which may be detected (and rejected) by measuring the pressure in the thorax. The evaluation may be in terms of a weighing algorithm, where an accepted signal gets a finite weight larger than zero, whereas a rejected signal segments gets the weight of zero. The accepted signal segment may use a weight of one for fully accepted signal segments and a smaller weight for a partly accepted signal segment. The evaluation algorithm may be implemented to disregard rejected nerve activity signal segments when generating the combined signal.

Similar rejection algorithms can be adapted to the processing of the ECG signals.

The signal treatment unit may further be programmed for synchronized alignment of the nerve activity signal segments to the trigger feature. Some of the activity in a nerve may be related to the heart beats in terms of phase. Information related to this cardiac related activity can be extracted from nerve activity signal recording by synchronized alignment of several activity signal segments.

The number of segments to be used may be defined by a fixed number or it may be defined to a fixed time interval. In addition, each segment may be weighted differently in the processing e.g. the most current segments may have the highest weight in the processing (by incorporating a forgetting factor), or the weights may be set according to an estimate of the noise in the segment, such that noisy segments are given less influence on the result. In addition, the number of segments to include in the process may be adaptively defined, for example by basing it on the noise level in the individual segments or in the combined signal. In this way the system would adapt to periods of low noise level by decreasing the numbers of segments used for making the combined signal, meaning that seizures could be predicted earlier compared to when noise levels were high.

The activity related feature may further be based on one or more input values from additional measurements either from measuring modalities internal to the device itself or from measuring modalities communicatively connected to the device. The input values may relate to such values as ECG features, EMG features, acceleration of the device, orientation of the device, temperature, pressure, oxygen saturation, carbon dioxide level, pH level, adrenalin level, and level of anti-epileptic drug(s), etc. The input value may also be based on two or more activity related features, and on activity related features deduced from more than one neural activity signal. The input value may be selected based on a classification process where the ability of further improving the detection of a specific behaviour of the cardiac related neural activity has been evaluated.

The device or at least part of the device may be provided in a material suitable for implantation, which means that it has to be minimally damaging for the body and at the same time be able to protect the interior of the device. Examples of materials which may be suitable are metals and metal alloys such as aluminium, titanium stainless steels, cobalt-chromium alloys, silicones, polyurethanes, polymethacrylates, poly (ethylene terephthalate), polypropylene, polyethylene, polytetrafluoroethylene (vascular prostheses), polyamides, polylactides, poly(glycolic acids) and ceramic materials. In embodiments, an outer surface of the device is coated with a suitable material for implantation.

The device may further be communicatively connected to at least one treatment modality, e.g. a vagus nerve stimulator or a drug pump. It may, however, also be able to control treatment modalities elsewhere inside or outside the body of the patient. The control of treatment modality may be graded e.g. so that a small seizure probability initiates a mild treatment scheme, and an increase in seizure probability will cause the use of a progressively aggressive treatment scheme.

The invention may also control an alarm, which informs the patient or health care personnel about a detected cardiac related neural activity with a specific behaviour. That is about the meeting or fulfilling of a predefined criterion, for example relating to a predicted or detected seizure or other disorder. The patient may be informed about a pending or forthcoming disorder via sound, electrical stimulation, vibration or other means of sensory stimuli from the implant itself or an external alarm device which communicates with the implant. Likewise the health care personnel, may be informed about an expected disorder via the alarm described above or, in addition, via a wireless communication link between the implant itself (or an external patient mounted communication device) and a healthcare information system.

One particular interesting cardiac related neural activity related disease, where the described device could be of special interest is epilepsy. Therefore, in a preferred embodiment the cardiac related neural activity described above may be related to an epileptic seizure.

Prediction of epileptic seizures is valuable for all persons suffering from epilepsy. Therefore in yet a preferred embodiment the device described above may be further programmed for when detecting the cardiac related neural activity to predict a forthcoming epileptic seizure.

The invention may also be used within the treatment of chronic heart failure or other heart conditions. Information about heart rate can be extracted from the ECG. Using the invention described above, cardio related activity concerning blood pressure may be obtained from a nerve which conduct baro receptors activity (pressure sensitive receptor which increases firing rate during high pressure) e.g. the vagus nerve (10th cranial nerve) or the glossopharyngeus nerve (9th cranial nerve). Another relevant measure which indicates the level of stress may be the cardiac related activity of sympathetic nerves which innervate the heart. A treatment modality may be used for lowering blood pressure and heart rate, when the extracted activity indicates a high blood pressure, high heart rate or an increased stress level. Treatment might be performed by e.g. the release of drugs or electrically stimulating the vagus nerve or a branch of it.

The device may be scheduled to switch between scheduled and on-demand treatment e.g. during the night scheduled treatment (open loop treatment) may be performed and during the day close loop treatment may be performed.

The device may be able to store recordings e.g. either by manual triggering (via an external device), by setting it to store recordings prior to and during detected seizures or by scheduled recordings. Recordings, settings and state of implant may be retrieved from the device via wireless communication, with an external communication device. Recordings may be used by health care personnel to evaluate current state of the patient (e.g. frequency, duration and time of day for the occurrence of seizures) this may be relevant for adjusting the treatment scheme of the patient. In addition based on the recordings, the activity related feature and criteria may be adjusted (via the external device).

The implant may be battery powered in a manner similar to other implantable devices.

In second and third aspects of the invention there is provided a computer program product, when in use on a computing unit, to cause a device to perform the below steps and a method for detecting cardiac related neural activity, the invention according to the second and third aspects is based on the steps:

receiving an ECG-signal and a nerve activity signal,
detecting a trigger feature in the ECG-signal,
in response to detecting a trigger feature, extracting a nerve activity signal segment from the nerve activity signal,
either generating a combined signal from a number of nerve activity signal segments, and
extracting an activity related feature from the combined signal,
or extracting a segment-based activity related feature from a number of nerve activity signal segments, thereby extracting a number of activity related features, and
generating an activity related feature by combining the segment-based activity related features; and
comparing the activity related feature to a predefined criterion and in the event of the activity related feature fulfils the predefined criterion, detecting the cardiac related neural activity.

The second and third aspects may be implemented into a device of the first aspect in order to provide a device with the functionality of these aspects.

In general, the individual aspects of the present invention may each be combined with any of the other aspects. These and other aspects of the invention will be apparent from the following description with reference to the described embodiments.

BRIEF DESCRIPTION OF THE FIGURES

Embodiments of the invention will be described, by way of example only, with reference to the drawings, in which.

DESCRIPTION OF EMBODIMENTS

The following description presents results based on scientific experiments directed to the prediction of epileptic seizures in rats. It is to be understood that the description is provided in order to illustrate an example of the use of the present invention. The invention is not limited to the use on animals as is clear to the skilled person.

Figure 1:
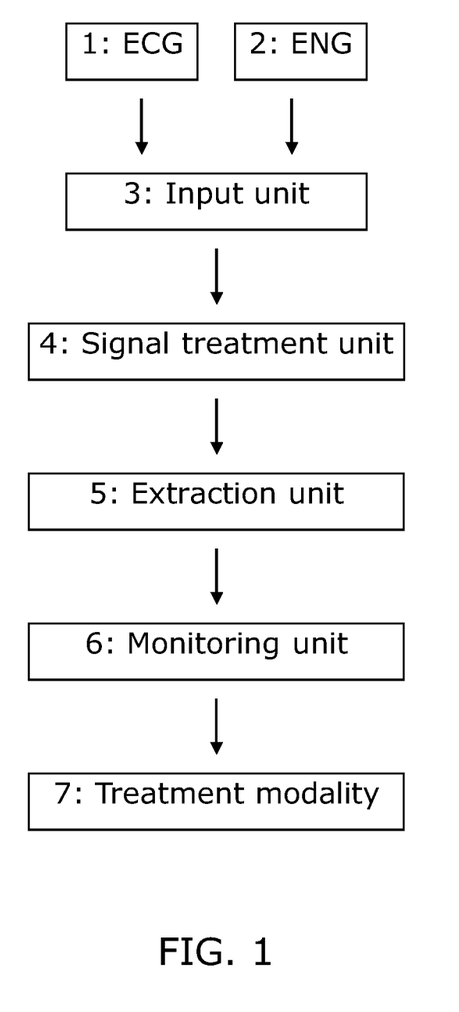
FIG. 1 shows a diagram of elements of a device for analyzing cardiac related neural activity.

FIG. 1 shows a diagram of elements of a device for analyzing cardiac related neural activity. In the following disclosure, the nerve activity signal is dealt with in terms of the vagus nerve activity signal, hereafter referred to as the vagus nerve ElectroNeuroGram, or simply as ENG.

The ECG and ENG signals 1, 2 are received at the input unit 3. The ENG signals can be received using vagus nerve electrodes. ECG signals can be obtained by standard means. The input unit sends the received signals to a signal treatment unit 4 which in an embodiment processes the signals in the following order: a) detect a trigger feature in the ECG-signal; b) the trigger feature is then used to extract a nerve activity signal segment from the ENG signal. After having extracted a number of nerve activity signal segments, an activity related feature is extracted in an extraction unit 5. In one embodiment, the activity related feature is extracted based on a combined signal. In another embodiment, the activity related feature is extracted from the nerve activity signal segments. This activity related feature can be calculated by predefined algorithms as explained below. The activity related feature is sent to the monitoring unit 6 where it is compared to a predefined criterion, and if it fulfils the criterion, a cardiac related neural activity is detected. In the case of detection of a cardiac related neural activity the monitoring unit may activate a treatment modality 7 which could be a drug pump or a vagus nerve stimulator.

Figure 2:
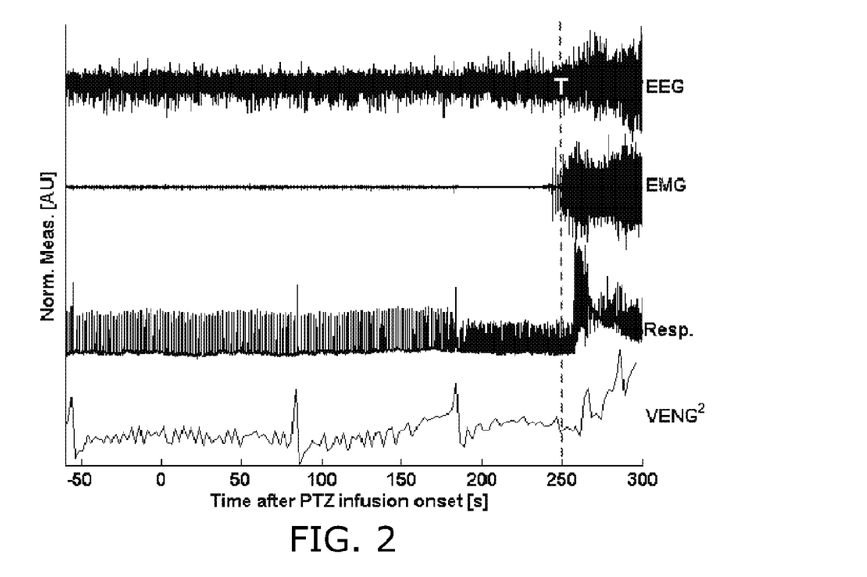
FIG. 2 shows signals recorded in an experimental study performed on anesthetized male rats.

Experimental results related to an animal study is presented in the following. The experimental results were based on inducing seizures in rats. The seizures were induced using pentylenetetrazol (PTZ) diluted in saline, which was infused at a rate of 10 mg/kg per min over 5 min. The study was performed on 14 anesthetized rats. The rats were divided into two groups: pentylenetetrazol (PTZ)-10 treated rats (n=8) and saline-treated controls (n=6). In the PTZ-treated group, tonic-clonic seizures were induced by administration of PTZ (50 mg/kg) diluted in saline and intravenously infused over a period of 5 min (24 ml/kg/h, total infused volume: 2 ml/kg). The control rats were infused with an equal volume of saline. The following signals were recorded: electroencephalogram (EEG), electrocardiogram (ECG), respiration, left and right vagus ENG (VENG) and electromyography (EMG). Some of these signals are shown in FIG. 2 showing 1 min of baseline and the 5 min. of PTZ infusion. In the EEG trace "T" indicates the start of a distinctive type of EEG activity which was asociated with the onset of tonic muscle activity. It can be seen that during the experiment there is a correlation between respiration activity and the vagus ENG ($VENG^2$). This is pronounced during the periodicly occuring events of deep breath (DB) and during the sustained expansion of the thorax during tonic seizure. The shown vagus ENG is from the left vagus nerve.

Figure 3:
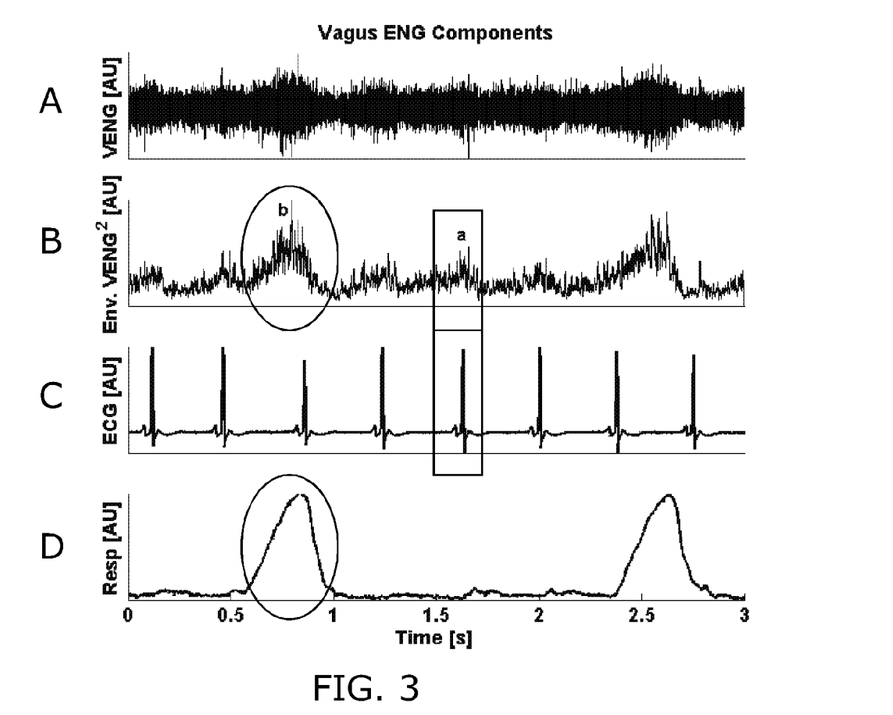
FIG. 3 shows additional signals obtained in the experimental study.

In FIG. 3 four plots are shown. FIG. 3A shows the vagus ENG (VENG) as detected, that is the nerve activity signal. This signal is pre-processed in order to extract the envelop of the vagus ENG power (Env. $VENG^2$) as shown in FIG. 3B. The combined signal is based on this signal. The ECG signal is shown in FIG. 3C and the respiration (Resp) is shown in FIG. 3D. Increases in the respiration trace indicate an expansion of the thorax. It is clear that some of the activity in the vagus ENG is related to the heart beat (a) (compare inserted squares which are positioned at the same place in the time line) and some is related to the respiration (b) (compare inserted ovals which are positioned at the same place in the time line). All FIGS. are on the same time scale as indicated by the time axis of FIG. 3D.

ECG and vagus ENG recordings were divided into consecutive periods of 20 s. For each of these periods, the vagus ENG was high pass filtered at 1 kHz, squared and filtered with a 5 ms moving average filter, resulting in the envelope of the VENG power (FIG. 3B). The R peaks of the ECG were used for triggering the synchronized averaging of the VENG power envelope.

For each trigger feature (R-peak) a nerve activity signal segment on both sides are extracted and combined. In the current embodiment, the signal is combined by use of an averaging.

Figure 4:
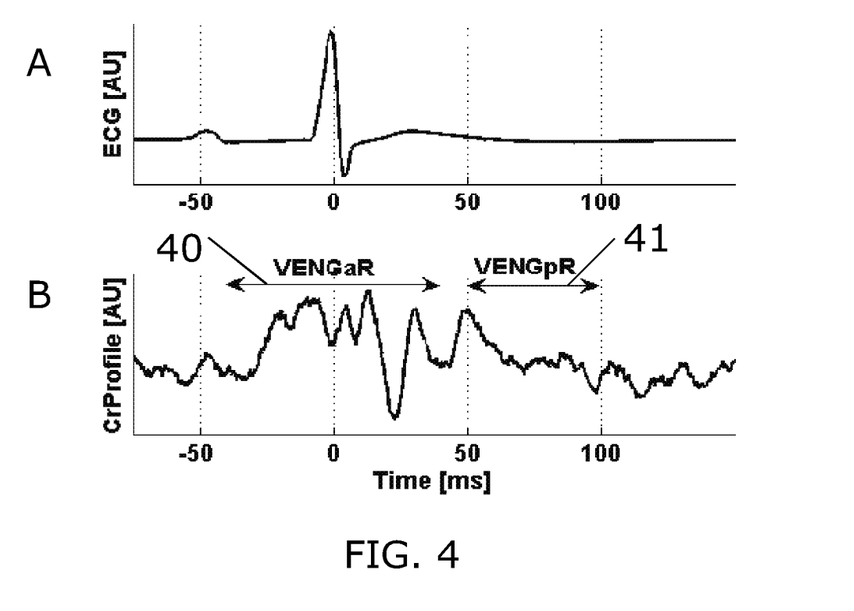
FIG. 4 illustrates averaged signals, in the form of an average ECG sweep and the combined signal.

FIG. 4 illustrates the result of the averaging procedure. FIG. 4A shows the average ECG sweep for several heart beat sweeps.

The combined signal is shown in FIG. 4B. This combined curve is hereafter referred to as the Cardiac Related profile (CrProfile). Such a profile is generated for each 20 s period. In the illustrated CrProfile two intervals were defined: (1) a 80 ms long interval centered on the R peak called "vagus ENG around R" (VENGaR) 40, (2) a 50 ms long interval located from 50 to 100 ms after the R peak which was called "Vagus ENG post R" (VENGpR) 41. The activity related features, here the vagus nerve feature (VNF), was extracted based on the formula:

$$VNF = mean(VENGpR) - mean(VENGaR) \quad (1)$$

Subtraction is used to make the feature less sensitive to fluctuation in the general level of VENG, caused e.g. by changes in the respiration pattern. The standard deviation of VNF baseline (SDBase) was estimated from a 3 min baseline recording. The mean VNF (meanBase) was estimated from the 1 min baseline immediate prior to the onset of PTZ infusion. The normalized VNF (VNFNorm) was then defined as:

$$VNFNorm = (VNF - meanBase)/SDBase \quad (2)$$

A seizure can be defined as detected when VNFNorm increased to more than a predefined criterion. In an embodiment, the predefined criterion may be set as a number of standard deviations from baseline. The predefined criterion may also be set based on control group results.

The location and duration of the intervals VENGpR and VENGaR can be optimized, e.g. using Pearson Correlation, to quantify the ability of the VNFNorm to separate PTZ-treated animals from control group animals. The optimization results in that VENGaR should optimally be selected as a 30 ms long interval centered at 5 ms after the R peak, and VENGaR should optimally be selected as a 50 ms long interval centered at 115 ms after the R peak. Moreover, the correlation revealed that the activity related features is most suited to be based on the nerve activity signals obtained from the left vagus nerve.

Figure 5:
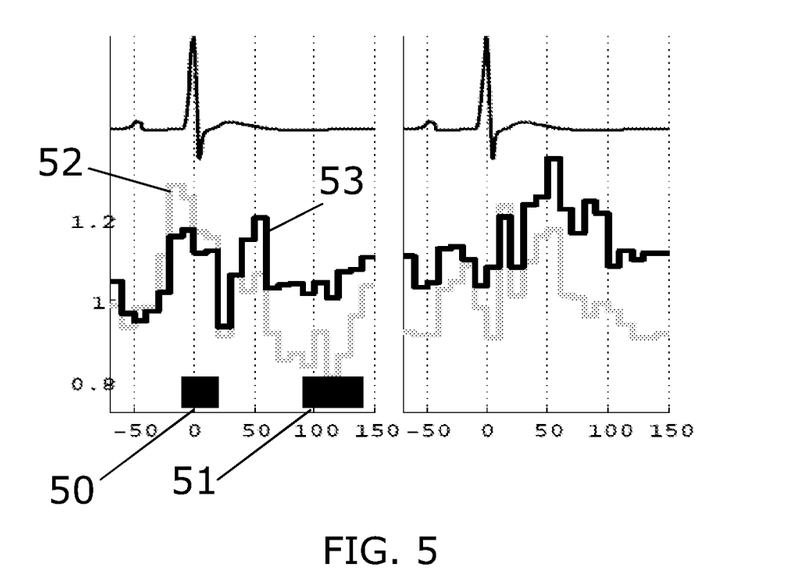
FIG. 5 illustrates the process of generating the combined signal.

FIG. 5 illustrates another example of generation the combined signal. The figure shows the result for the left vagus nerve on the left and the right vagus nerve on the right. Similarly to FIG. 4A, average ECG sweeps are shown on top of the combined signals. The figure show light traces 52 corresponding to data obtained prior to PTZ injection, i.e. corresponding to baseline data, and dark traces based on data from 60 sec. to 40 sec. prior to seizure onset. Moreover, as compared to the combined signal of FIG. 4B, the data has been down-sampled by including only one data point for each 10 ms period, corresponding to the power within this period. Due to the down-sampling, the combined signals of FIG. 5 can be more efficiently dealt with computationally than the combined signal of FIG. 4B. The black boxes indicate the location of the optimized VENGaR 50 and VENGpR 51.

Figure 6:
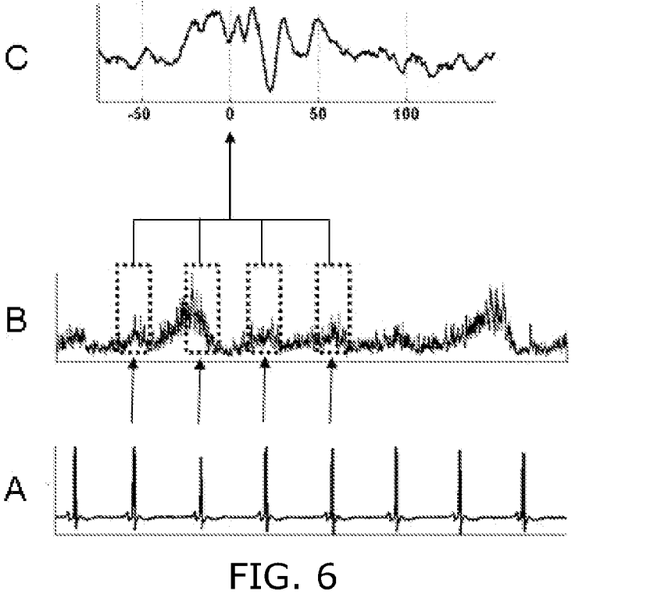
FIG. 6 illustrates averaged signals, in the form of an average ECG sweep and the combined signal.

FIG. 6 further illustrates the process of generating the combined signal. FIG. 6A illustrates the ECG-signal of FIG. 3C. For each detected trigger feature (here exemplified by four features), e.g. each detected R-peak, a signal segment of the nerve activity signal is extracted. This is exemplified in FIG. 6B by the signal segments comprised in the boxes. FIG. 6B is the pre-processed vagus nerve signal of FIG. 3B. The extracted signals are combined into a single combined signal in FIG. 6C, here exemplified by the averaged signal of FIG. 4B.

In another embodiment, the combined signal need not be generated. From each of the signal segments (FIG. 6B), the activity related feature (VNFNorm) is extracted. These segment-based features are combined to form a combined activity related feature. For example to form a combined VNFNorm.

Figure 7:
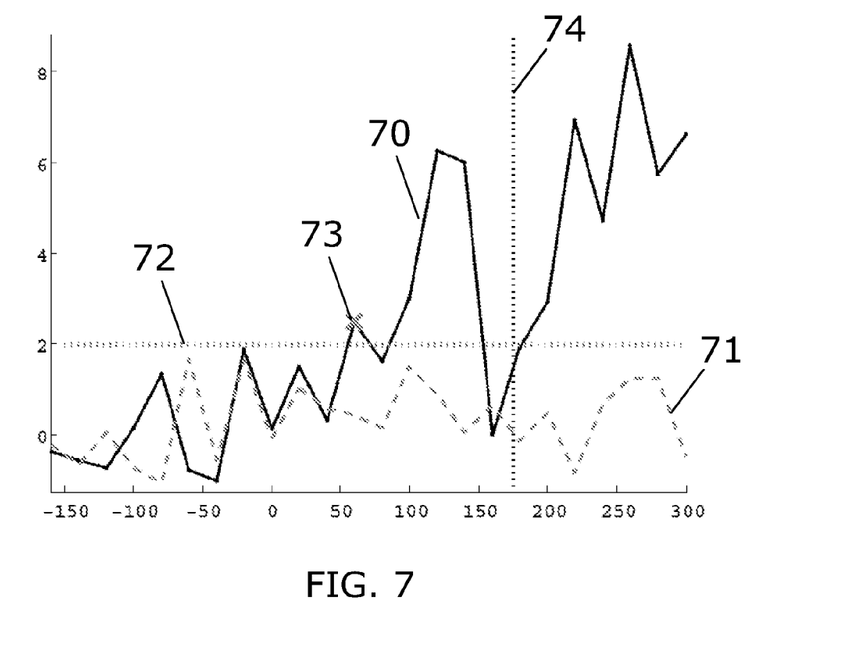
FIG. 7 shows the development of the normalized vagus nerve feature.

FIG. 7 shows the development of the normalized vagus nerve feature (vertical axis) as a function of time in seconds (horizontal axis). The figure illustrates the development for PTZ infused rats 70 and for the control group rats 71. The PTZ/saline was infused at 0 sec. The optimized intervals for the VENGpR and VENGaR intervals were used. The prediction threshold 72 is set to be just higher than the highest baseline value obtained in the control group rats. A seizure may be define in various ways. One way of defining a seizure is to relate the seizure to the EEG activity ranging from stage S0 which is relating to baseline activity to stage S3 which relates to tonic seizure. The stage S2 may be regarded as a precursor to tonic seizure. The onset of the S2-stage is shown in the figure by reference numeral 74. Seizures were regarded as "early detected", if they were detected based on VENG before the onset of stage S2. On the average, a seizure 73 is detected 84±35 55 s prior to stage S2 and 103±35 51 s prior to stage S3. No control group rats were observed to pass the threshold 72 after injection of saline. The results indicate a 100% sensitivity and specificity of the method. It is within the capability of the skilled person to select the positioning of a threshold in connection with human patients.

Figure 8:
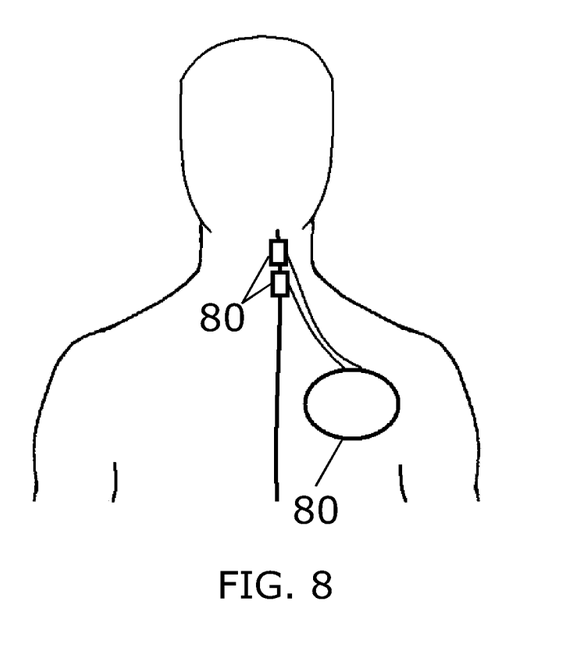
FIG. 8 schematically illustrates a device according to an embodiments of the invention.

FIG. 8 shows a device according to an embodiment of the invention. The device is implanted in the body of a human. The device comprises a central unit 80 and two electrodes 81. One electrode for sensing the vagus nerve activity signal and another for stimulating the vagus nerve in the event a specific activity related feature is detected. The sensing electrode and the stimulating electrode may be a single electrode with both functionalities. The device may be provided as a suitable unit adapeted to operate in an autonome manner once it has been implanted into a patient.

The invention can be implemented by means of hardware, software, firmware or any combination of these. In particular the invention may comprise programmable units that may be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claim is:

1. A device for detecting a cardiac related neural activity indicative of a neural disorder or seizure and for treating the neural disorder or seizure, the device being implantable into a body of a patient and comprising:
    an input unit for receiving an ECG-signal and a nerve activity signal;
    a signal treatment unit programmed for:
        detecting a trigger feature in the ECG-signal,
        in response to detecting a trigger feature, extracting a nerve activity signal segment from the nerve activity signal,
    an extraction unit programmed for:
        extracting a segment-based activity related feature from a number of nerve activity signal segments, thereby extracting a number of activity related features and
        generating an activity related feature by combining the segment-based activity related features;
    a monitoring unit programmed for:
        comparing the activity related feature to a predefined criterion and in the event of the activity related feature fulfils the predefined criterion, detecting the cardiac related neural activity indicative of a neural disorder or a seizure; and
    means for treating the neural disorder or seizure in the form of a nerve stimulator or a drug pump.

2. The device according to claim 1, wherein the predefined criterion is adaptively refined.

3. The device according to claim 1, wherein the signal treatment unit is further programmed for evaluating the nerve activity signal segment by use of an evaluation algorithm, and in accordance with an output of the evaluation algorithm accepts or rejects the nerve activity signal segment.

4. The device according to claim 1, wherein the signal treatment unit is further programmed for synchronized alignment of the nerve activity signal segments to the trigger feature.

5. The device according to claim 1, wherein the signal treatment unit is further programmed for weighing each nerve activity signal segments.

6. The device according to claim 1, wherein the activity related feature is further based on an input value.

7. The device according to claim 1, wherein the nerve activity signal is obtained by an electrode, where the vagus nerve stimulator is an electrode and where the nerve activity signal obtaining electrode is one and the same as the vagus nerve stimulator electrode.

8. The device according to claim 1, wherein the device is communicatively connected to an alarm unit.

9. A device for detecting a cardiac related neural activity indicative of a neural disorder or seizure and for treating the neural disorder or seizure, the device being implantable into a body of a patient and comprising:
- an input unit for receiving an ECG-signal and a nerve activity signal;
- a signal treatment unit programmed for:
  - detecting a trigger feature in the ECG-signal,
  - in response to detecting a trigger feature, extracting a nerve activity signal segment from the nerve activity signal,
- an extraction unit programmed for:
  - generating a combined signal from a number of nerve activity signal segments and
  - extracting an activity related feature from the combined signal;
- a monitoring unit programmed for:
  - comparing the activity related feature to a predefined criterion and in the event of the activity related feature fulfils the predefined criterion, detecting the cardiac related neural activity indicative of a neural disorder or a seizure, and
- means for treating the neural disorder or seizure in the form of a nerve stimulator or a drug pump.

10. The device according to claim 9, wherein the signal treatment unit is further programmed for pre-processing the nerve activity signal and to base the combined signal on the pre-processed nerve activity signal.

11. The device according to claim 9, wherein the combined signal is generated by a functional mapping of the number of signal segments to the combined signal.

12. A method for detecting a cardiac related neural activity indicative of a neural disorder or a seizure, the method comprising:
- receiving an ECG-signal and a nerve activity signal,
- detecting a trigger feature in the ECG-signal,
- in response to detecting a trigger feature, extracting a nerve activity signal segment from the nerve activity signal,
- either
  - generating a combined signal from a number of nerve activity signal segments, and
  - extracting an activity related feature from the combined signal, or
  - extracting a segment-based activity related feature from a number of nerve activity signal segments, thereby extracting a number of activity related features, and
  - generating an activity related feature by combining the segment-based activity related features; and
- comparing the activity related feature to a predefined criterion and in the event of the activity related feature fulfils the predefined criterion, detecting the cardiac related neural activity indicative of a neural disorder or a seizure, the method further comprising the step of activating means for treating the neural disorder or seizure.

13. A method according to claim 12, wherein the nerve activity signal is obtained from the vagus nerve.

14. A method according to claim 12, wherein the nerve activity signal is obtained from an electrode and the means for treating the neural disorder or seizure is a vagus nerve stimulator, and where said electrode and vagus nerve stimulator are one and the same.

* * * * *